(12) United States Patent
Jhangiani

(10) Patent No.: US 10,716,714 B2
(45) Date of Patent: Jul. 21, 2020

(54) SOILED DIAPER DETECTION SYSTEM

(71) Applicant: 5TECH LLC, Berkeley, CA (US)

(72) Inventor: Rohit Jhangiani, Berkeley, CA (US)

(73) Assignee: 5TECH LLC, Berkeley, CA (US)

( * ) Notice: Subject to any disclaimer, the term of this patent is extended or adjusted under 35 U.S.C. 154(b) by 0 days.

(21) Appl. No.: 15/909,927

(22) Filed: Mar. 1, 2018

(65) Prior Publication Data
US 2018/0250174 A1 Sep. 6, 2018

Related U.S. Application Data

(60) Provisional application No. 62/466,024, filed on Mar. 2, 2017, provisional application No. 62/468,298, filed on Mar. 7, 2017.

(51) Int. Cl.
| | | |
|---|---|---|
| *A61F 13/42* | (2006.01) | |
| *G08B 21/20* | (2006.01) | |
| *A61F 13/84* | (2006.01) | |
| *A61F 5/48* | (2006.01) | |
| *A61B 5/00* | (2006.01) | |

(52) U.S. Cl.
CPC .............. *A61F 13/42* (2013.01); *G08B 21/20* (2013.01); *A61B 5/0015* (2013.01); *A61B 5/6808* (2013.01); *A61B 2562/029* (2013.01); *A61F 5/48* (2013.01); *A61F 2013/421* (2013.01); *A61F 2013/424* (2013.01); *A61F 2013/8479* (2013.01)

(58) Field of Classification Search
CPC ...... A61F 13/42; A61F 2013/424; A61F 5/48; A61F 2013/421; A61F 2013/8479; G08B 21/20; A61B 5/0015
See application file for complete search history.

(56) References Cited

U.S. PATENT DOCUMENTS

| | | | |
|---|---|---|---|
| 5,469,145 A | | 11/1995 | Johnson |
| 5,568,128 A | * | 10/1996 | Nair ........................ A61F 5/48 |
| | | | 128/885 |
| 5,959,535 A | | 9/1999 | Remsburg |
| 6,627,786 B2 | * | 9/2003 | Roe ........................ A61F 13/42 |
| | | | 604/361 |
| 8,471,715 B2 | | 6/2013 | Solazzo |
| 8,664,467 B2 | * | 3/2014 | Roe ........................ A61F 13/42 |
| | | | 128/886 |

(Continued)

FOREIGN PATENT DOCUMENTS

| | | |
|---|---|---|
| JP | 2000093448 A | 4/2000 |
| WO | 2014122169 A1 | 8/2014 |
| WO | WO-2014122169 A1 * | 8/2014 .............. A61F 13/42 |

OTHER PUBLICATIONS

Opro9, "Opro9 SmartDiaper" (http://www.opro9.com/opro9/FHH201/index.html), (Accessed Jul. 26, 2018).

(Continued)

*Primary Examiner* — Adnan Aziz
(74) *Attorney, Agent, or Firm* — Cognition IP, P.C.; Bryant Lee

(57) ABSTRACT

A soiled diaper detection system having a soiled diaper detection device, one or more computer devices in communication with the diaper detection device configured to generate and process requests to the diaper detection device, and store data received from the soiled diaper detection device.

15 Claims, 10 Drawing Sheets

(56) References Cited

U.S. PATENT DOCUMENTS

| | | | |
|---|---|---|---|
| 9,671,383 B2* | 6/2017 | Ansley | G01N 33/0075 |
| 9,675,497 B1 | 6/2017 | Levin | |
| 10,028,865 B2* | 7/2018 | Krasnow | A61F 13/42 |
| 2001/0021833 A1* | 9/2001 | Schmidt | A61F 13/475 |
| | | | 604/385.01 |
| 2003/0011479 A1* | 1/2003 | Bluteau | A61F 13/42 |
| | | | 340/573.5 |
| 2004/0236302 A1* | 11/2004 | Wilhelm | A61F 13/42 |
| | | | 604/389 |
| 2005/0156744 A1* | 7/2005 | Pires | A61F 13/42 |
| | | | 340/573.5 |
| 2007/0252713 A1* | 11/2007 | Rondoni | A61B 5/202 |
| | | | 340/573.5 |
| 2008/0198007 A1* | 8/2008 | Chi-Jung | G08B 25/14 |
| | | | 340/540 |
| 2008/0278336 A1* | 11/2008 | Ortega | A61B 5/1113 |
| | | | 340/573.5 |
| 2008/0300470 A1* | 12/2008 | Gerber | A61B 5/1116 |
| | | | 600/301 |
| 2009/0326417 A1* | 12/2009 | Ales, III | A61F 13/42 |
| | | | 600/584 |
| 2010/0164733 A1* | 7/2010 | Ales | A61F 13/42 |
| | | | 340/604 |
| 2010/0277324 A1* | 11/2010 | Yeh | A61F 13/42 |
| | | | 340/573.5 |
| 2012/0035496 A1* | 2/2012 | Denison | A61B 5/053 |
| | | | 600/547 |
| 2012/0206265 A1* | 8/2012 | Solazzo | A61F 13/42 |
| | | | 340/573.5 |
| 2013/0110061 A1 | 5/2013 | Abraham et al. | |
| 2014/0200538 A1* | 7/2014 | Euliano | A61F 13/42 |
| | | | 604/361 |
| 2014/0266735 A1 | 9/2014 | Riggio et al. | |
| 2014/0292520 A1* | 10/2014 | Carney | G06F 19/3418 |
| | | | 340/573.5 |
| 2016/0158071 A1* | 6/2016 | Barda | A61F 13/42 |
| | | | 604/361 |
| 2016/0278692 A1 | 9/2016 | Larson et al. | |
| 2017/0035622 A1* | 2/2017 | Wang | A61F 13/42 |
| 2017/0156594 A1* | 6/2017 | Stivoric | A61B 5/7275 |
| 2017/0186446 A1* | 6/2017 | Wosk | G10L 25/78 |
| 2018/0055697 A1* | 3/2018 | Mihali | A61F 13/42 |
| 2018/0149635 A1* | 5/2018 | Abir | A61F 5/44 |

OTHER PUBLICATIONS

Opro9, "Opro9", (https://www.opro9.com/opro9/index.php/en/), (Accessed Jul. 26, 2018).

Omonit, "Omonit Smart Baby Care", (http://goodmonit.com/), (Accessed Jul. 26, 2018).

Non-Final Office Action dated Aug. 28, 2018 for U.S. Appl. No. 15/953,405; 14 pages.

Final Office Action dated Mar. 8, 2019 for U.S. Appl. No. 15/953,405; 19 pages.

* cited by examiner

SOILED DIAPER DETECTION SYSTEM

FIELD OF THE APPLICATION

This application relates to diapers, more specifically a soiled diaper detection system.

BACKGROUND

There are more than 3 million cases of diaper rash (diaper dermatitis) in the US every year. One of the main causes of diaper rash is prolonged exposure to urine or stool which can irritate the diaper wearer's sensitive skin. Moreover, being in soiled diapers for an extended period of time may cause urinary infections, bed sores (decubitus sores/decubitus ulcers). To mitigate diaper rash, urinary infections and bed sores in babies, adults, pets it may be desirable to try to ensure that the diaper wearers are not in soiled diapers for too long.

SUMMARY

The present disclosure may provide a soiled diaper detection system comprising of a soiled diaper detection device (also referred to as the 'detection device'), a computer device to manage the detection device, a computer device to process the data and a data storage system to store the data. The detection device may comprise one or more sensors such as gas sensors, humidity sensors, temperature sensors, wetness sensors, load or weight sensors, force sensors, along with one or more of a stick-on layer, a stick-on strap, and a clip-on mechanism that may be configured to removably attach the detection device easily to and from a diaper. In some example implementations, the stick-on layer, stick-on strap, or clip-on mechanism may be reusable and replaceable. The detection device may be configured to send a signal (e.g., a wireless signal) to a computer device, based on a change or rate of change in sensor readings (e.g., a change in humidity sensor readings, gas sensor readings, temperature sensor readings, wetness sensor readings, load or weight sensor readings, force sensor readings) that is greater than or equal to a configurable threshold value.

BRIEF DESCRIPTION OF DRAWINGS

The accompanying drawings, which are incorporated in and form a part of this specification, illustrate embodiments of the soiled diaper detection system and together with the description, serve to explain the aspects of this system.

DETAILED DESCRIPTION OF EMBODIMENTS

In order to reduce the time a diaper wearer sits in a soiled diaper, some example implementations of the present application may include a sensor that is configured to detect when a diaper has become soiled and to generate a notification, such as a notification to a caregiver, that a change of the diaper may be required.

Example implementations of the present application may relate to potential mechanisms to reduce diaper rash, urinary infections, bed sores using Internet of Things (IoT) devices that may work with various types of diapers with varying quantities of urine and stool.

Figure 1:
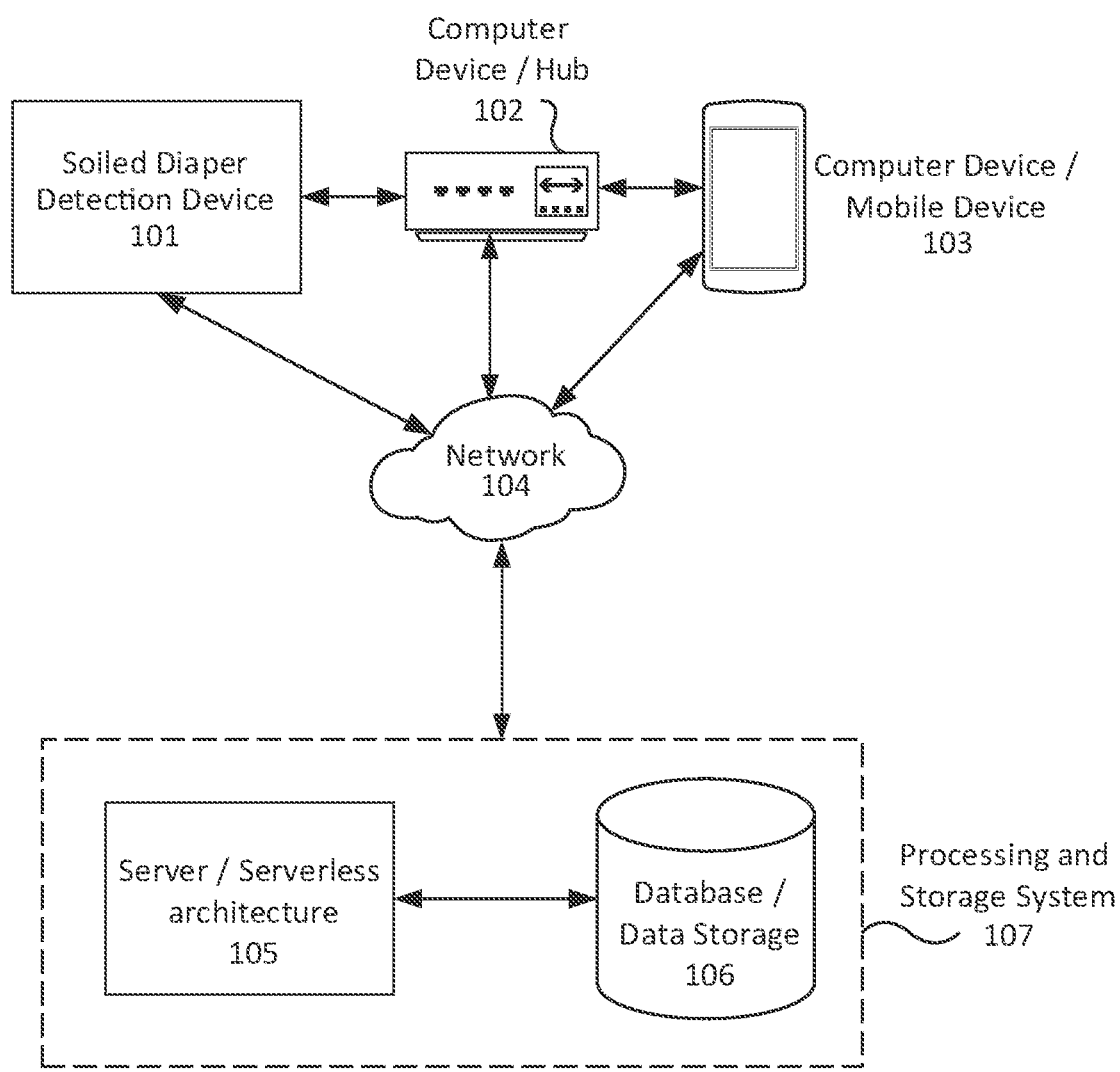
FIG. 1 illustrates a system network diagram with a soiled diaper detection device that may be configured wirelessly by a mobile device or a computer device, which may use optional auxiliary computer systems for processing and storing data according to example implementations of the present application.

FIG. 1 depicts a system network diagram with a diaper detection device 101 that may be configured wirelessly by a computer device 103 (referred to herein as 'the client'). A computer device 103 may be a mobile device such as a smartphone, tablet, watch, smart speaker, smart device or other computer device such as a laptop, desktop, server, thin-client, etc. running an application, such as a web application. Information such as configuration information, application information, user information, system information and any other information may be retrieved from or stored into a database 106 or a storage system such as a file storage system (collectively referred to herein as 'the data store') via a computer device such as a server or server less framework 105. The detection device 101 may send data via wireless signals over a network 104 to the client 103 and/or to another optional computer device 102 such as a computer or a hub which may then be transferred and stored in the data store. The client 103 and/or a computer or a hub 102 may send a wireless signal to the computer device such as a processing and storage system 107 that then retrieves the information from the data store 106. Some information may also be stored or cached on the client 103. Some embodiments use a hub between the detection device 101 and the client 103, while other embodiments do not use a hub and instead perform direct communication between the detection device 101 and the client 103 and/or the detection device 101 and a computer device such as a processing and storage system 107. In the embodiments that use a hub, the hub may send a wireless signal to and/or perform direct communication between the hub and a computer device such as a processing and storage system 107. The detection device 101 may connect to the client 103 or another computer 102 via Wi-Fi, Bluetooth low energy, Bluetooth, ZigBee, cellular data network or any other wireless communication method. The data from the detection device 101 and/or data provided by the user may be used by a learning-based system to adapt the device 101 to the diaper wearer and to the type of diaper.

The learning-based system may be hosted on the detection device, the client, or another computer or hub. The learning-based system may produce different outputs regarding whether a diaper change is required depending on the identity of the diaper wearer and the type of diaper. The learning-based system may be a machine learning based system using learning that is trained using input data such as (a) sensor data from one or more sensors such as a gas sensor, a humidity sensor, a temperature sensor, a wetness sensor, a load or weight sensor, and a force sensor and/or (b) the identity of the diaper wearer and/or (c) urination and defecation patterns of the diaper wearer and/or (d) the type of diaper. The learning-based system may increase accuracy of detection for particular diaper wearers and/or types of diapers.

In an alternate embodiment, the detection device may be connected to another computer device via the Internet, cellular network, GPS or any other wireless or satellite technology.

Figure 2:
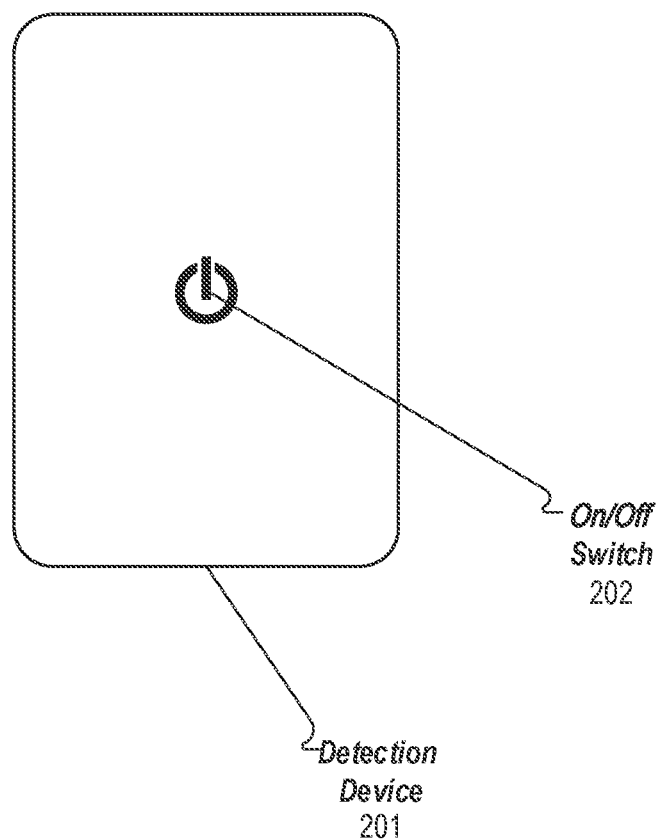
FIG. 2 illustrates a front view of the detection device that may have an on/off switch.

FIG. 2 illustrates a front view of the detection device 201 may have an on/off switch 202 that may be used to turn on or off or sleep the soiled diaper detection. When the detection device 201 is on, the detection device 201 may monitor the diaper for changes of state (e.g., not soiled→soiled) and when the detection device is off, the detection device 201 may not monitor the diaper for changes of state.

In an alternate embodiment, the detection device may be turned on or off from a computer device.

Figure 3:
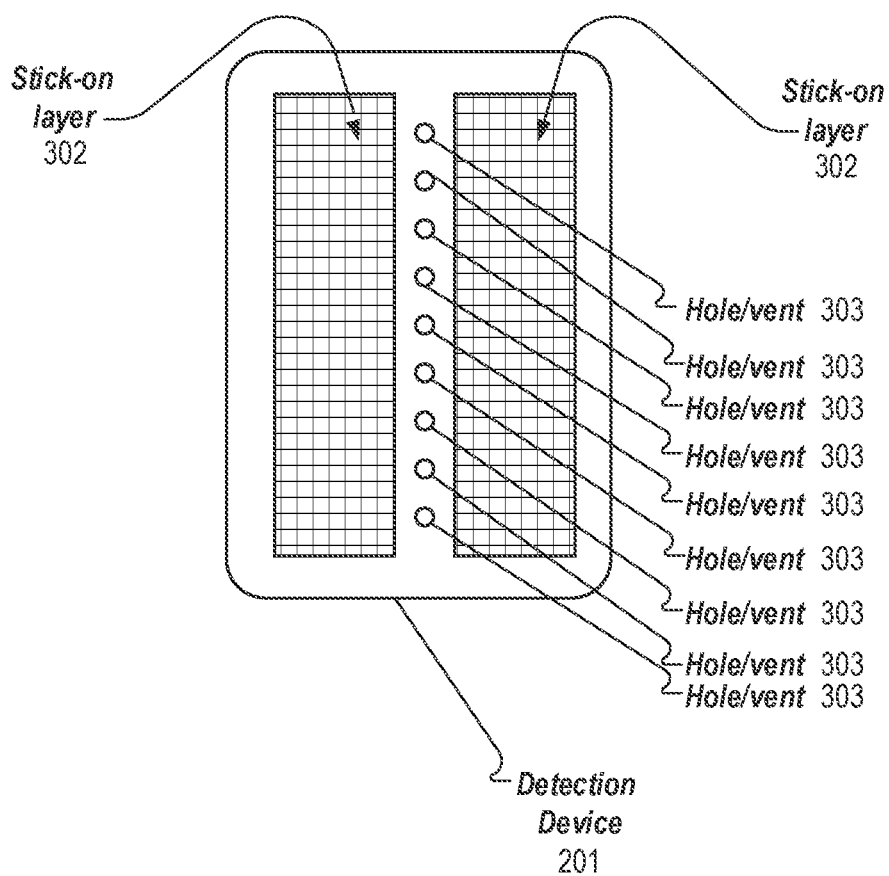
FIG. 3 illustrates a back view of the detection device that may have a reusable and/or replaceable stick-on layer that may enable the detection device to be removably attached to a diaper.

FIG. 3 illustrates a back view of the detection device 201 that may have a reusable and/or replaceable stick-on layer 302 that may enable the detection device 201 to be removably attached to a diaper. In some example implementations, the stick-on layer 302 may be reused several times over an extended period of time such as one or more years. In some example implementations, the stick-on layer 302 may be removed and replaced with a new stick-on layer. In such implementations, the stick-on layer 302 may be removably attached to the diaper. The detection device may also have one or more vents or holes 303.

Figure 4:
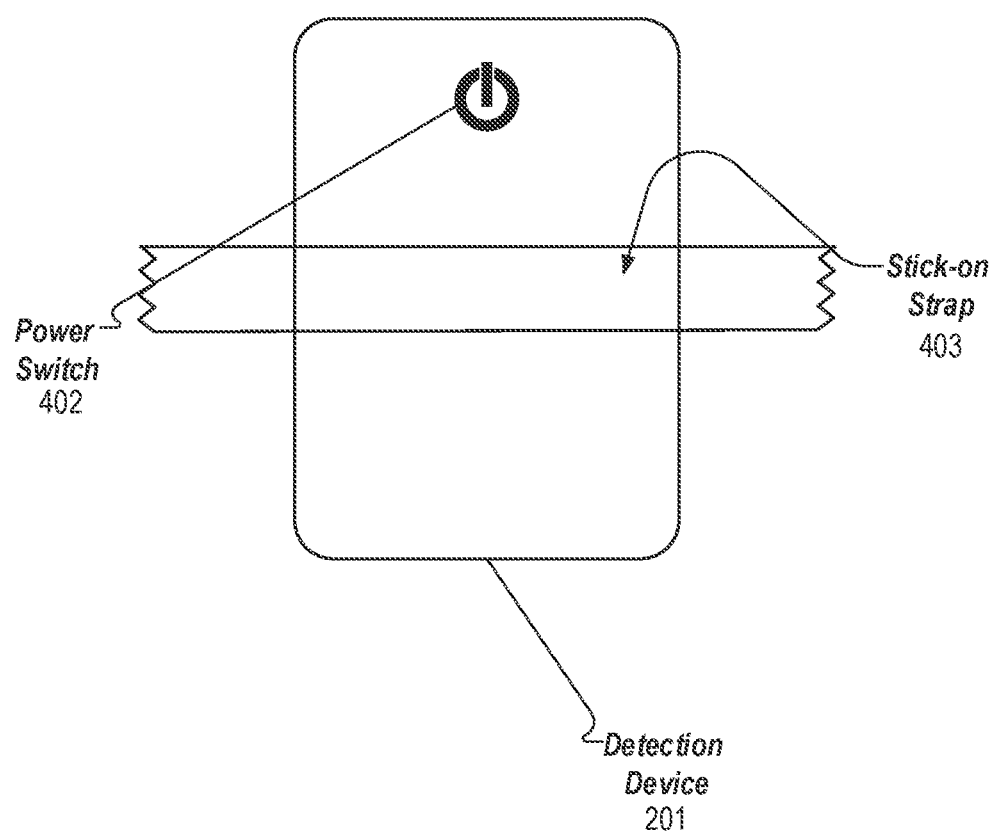
FIG. 4 illustrates a front view of the detection device that may have reusable and/or replaceable stick-on straps that may enable the detection device to be removably attached to a diaper.

FIG. 4 illustrates a front view of the detection device 201 that may have reusable and/or replaceable stick-on straps 403 that may enable the detection device to be removably attached to a diaper. The straps 403 may comprise of stick-on material that sticks onto the diaper. Using two straps (e.g., a left strap and right strap) may ensure that the detection device securely sticks on to the diaper. The straps 403 may be reused several times over an extended period of time such as one or more years. In some example implementations, the stick-on material on the straps may be removed and/or replaced. In such implementations, the stick-on material may be removably attached to the straps. In other example implementations, the straps 403 may be removed and replaced. In such implementations, the straps 403 may be removably attached to the diaper. In other example implementations, there may be one reusable and/or replaceable stick-on strap or more than two reusable and/or replaceable stick-on straps, such as four straps.

Figure 5:
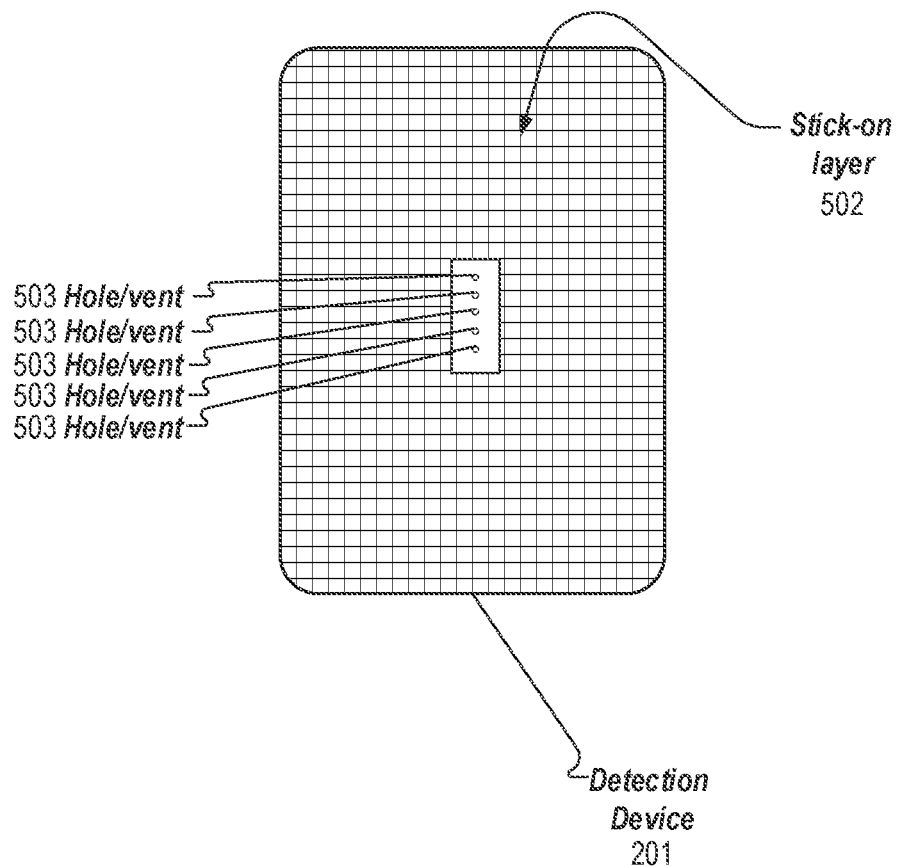
FIG. 5 illustrates a back view of the detection device that may have a reusable and/or replaceable stick-on layer along with one or more vents or holes that may enable the detection device to measure parameters using one or more sensors such as a humidity sensor, gas sensor, temperature sensor, wetness sensor, load or weight sensor, and force sensor. The reusable and replaceable stick-on layer may enable the detection device to be removably attached to the diaper.

FIG. 5 illustrates a back view of the detection device 201 that may have a reusable and/or replaceable stick-on layer 502 along with one or more vents or holes 503 that may enable the detection device to measure parameters using one or more sensors such as a humidity sensor, gas sensor, temperature sensor, wetness sensor, load or weight sensor, and force sensor. The reusable and replaceable stick-on layer 502 may enable the detection device to be removably attached to the diaper.

In an alternate embodiment, the sensors and other components may be fabricated on a stick-on layer or an adhesive material that may enable the detection device to be removably attached to the diaper.

Figure 6:
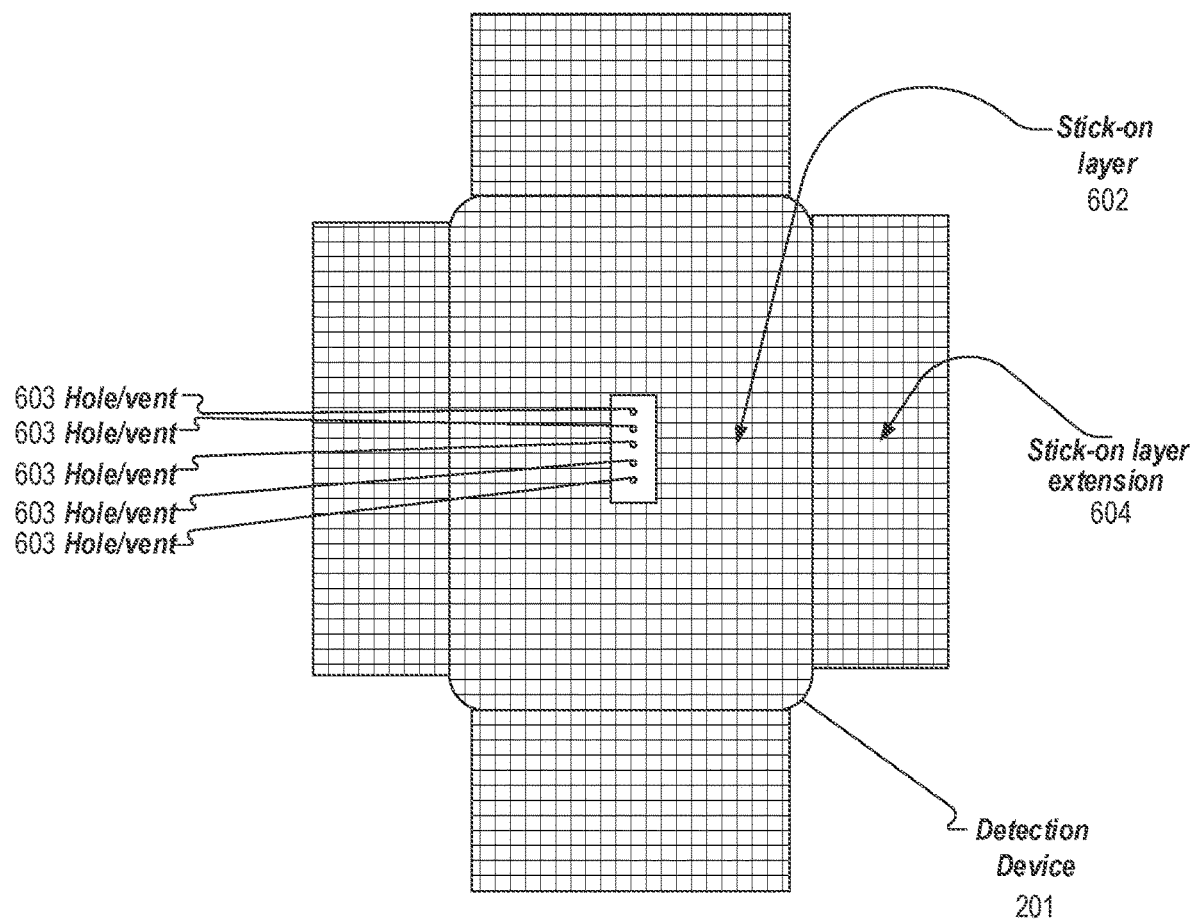
FIG. 6 illustrates a back view of the detection device that may have a reusable and/or replaceable stick-on layer such as a hook and loop fastener (e.g., Velcro) such that the stick-on layer extends from one or more sides such as two sides or four sides, along with one or more vents or holes that may enable the detection device to measure parameters using one or more sensors such as a gas sensor, humidity sensor, temperature sensor, wetness sensor, load or weight sensor, and force sensor. The reusable and replaceable stick-on layer may enable the detection device to be removably attached to the diaper.

FIG. 6 illustrates a back view of the detection device that may have a reusable and/or replaceable stick-on layer 602 that may have an stick-on layer extension 604 on one or more sides such as four sides along with one or more vents or holes 603 that may enable the detection device to measure parameters using one or more sensors such as a humidity sensor, gas sensor, temperature sensor, wetness sensor, load or weight sensor, and force sensor. The reusable and replaceable stick-on layer 602 and/or the stick-on layer extension 604 may enable the detection device to be removably attached to the diaper.

Figure 7:
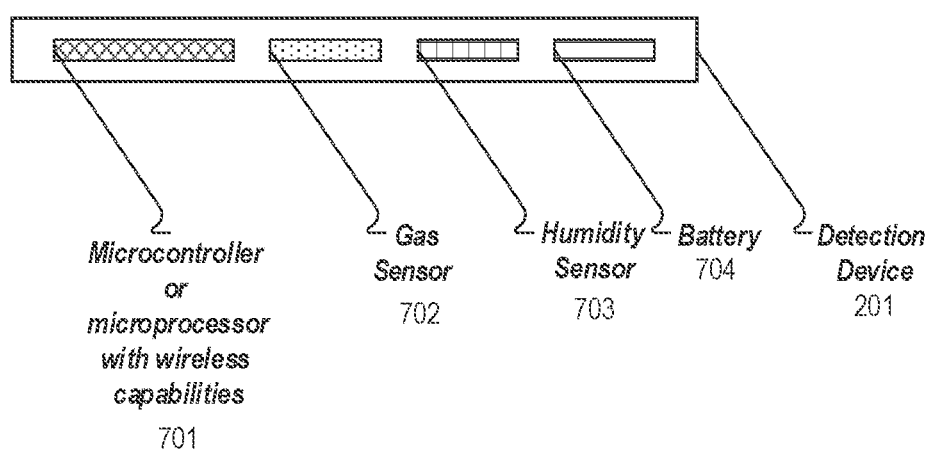
FIG. 7 illustrates a cross-section view of the detection device that may have one or more sensors such as a humidity sensor, a gas sensor, a temperature sensor, a wetness sensor, a load or weight sensor, and a force sensor.

FIG. 7 Illustrates a cross-section view of the detection device 201 that may have one or more sensors such as a gas sensor 702, a humidity sensor 703, a temperature sensor, a wetness sensor, a load or weight sensor, and a force sensor. The detection device 201 can be configured to send a wireless signal to a computer device when the concentration of one or more gases increases or when the rate of change of the concentration of gas increases by a configurable threshold amount or a configurable threshold percentage, such as a 5%, 10%, 1-5%, 2-5%, 5-10%, 10-20%, or 20-50% increase, in a very short amount of time, such as in 5, 10, 15, 30, 45, 60, 5-10, 15-30, or 30-60 seconds, and/or when the humidity increases by a configurable threshold amount or a configurable threshold percentage, such as a 5%, 10%, 1-5%, 2-5%, 5-10%, 10-20%, or 20-30% increase or when the rate of change of humidity increases above a configurable value in a very short amount of time, such as in 5, 10, 15, 30, 45, 60, 5-10, 15-30, or 30-60 seconds. Alternatively, in some example implementations, the detection device 201 may be configured to send a signal when the load or weight of the diaper increases by a configurable threshold amount, such as 0.05, 0.1, 0.2, 0.3, 0.4, or 0.5 ounces amount, or a configurable threshold percentage, such as 5%, 10%, 15%, 25%, 5-15%, 15-25%, 25-100%, or 100-400% in a very short amount of time, such as in 5, 10, 15, 30, 45, 60, 5-10, 15-30, or 30-60 seconds. The configurable threshold percentage may be a percentage of the default load or weight of the diaper.

In some embodiments, the gas sensor of the detection device 201 is in an off or low power mode until the humidity sensor is triggered, such as by humidity exceeding a threshold or rate of change of humidity exceeding a threshold in a short period of time. When the humidity sensor is triggered, then the detection device may then turn on one or more gas sensors on the device from the off or low power mode. This feature may be useful to save energy and extend battery life of the detection device.

Figure 8:
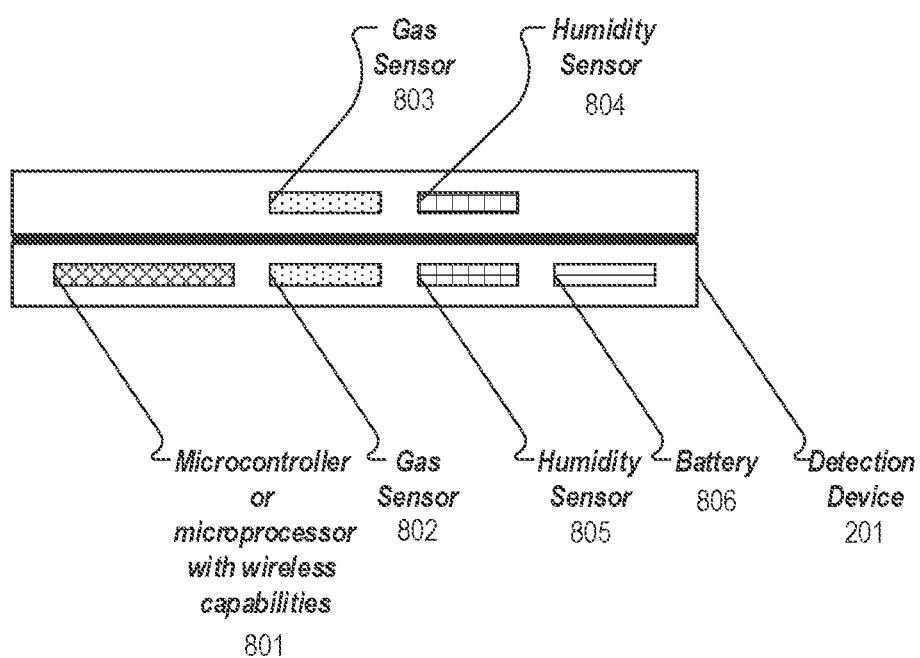
FIG. 8 illustrates a cross-section view of the detection device that may have two or more sensors such as gas sensors, humidity sensors, temperature sensors, wetness sensors, load or weight sensors, and force sensors that are separated by a layer such as a wireless signal blocking layer and/or a printed circuit board layer.

FIG. 8 illustrates a cross-section view of the detection device 201 that may have two or more sensors such as humidity sensors (804, 805), gas sensors (802, 803), temperature sensors, wetness sensors, load or weight sensors, and force sensors that are separated by a layer such as a wireless signal blocking layer and/or a printed circuit board layer. One set of sensors may face inside and towards the diaper, and may be configured to sense the concentration of gases, such as ammonia, methane and other gases, inside the diaper and measure other parameters, such as humidity, temperature, inside the diaper and the second set of sensors may face outside and away from the diaper, and may be configured to sense the concentration of gases, such as ammonia, methane and other gases, outside the diaper and measure other parameters, such as humidity, temperature, outside the diaper. The detection device may be configured to send a wireless signal to a computer device when the difference in concentration of gases measured between the inside and outside gas sensors is greater than a configurable threshold or a configurable threshold percentage, such as a 5%, 10%, 1-5%, 2-5%, or 5-10% increase, in a very short amount of time, such as in 5, 10, 15, 30, 45, 60, 5-10, 15-30, or 30-60 seconds, and when the difference in humidity measured between the inside and outside humidity sensors is greater than a configurable threshold or a configurable threshold percentage, such as a 5%, 10%, 1-5%, 2-5%, or 5-10% increase or when the rate of change of humidity increases above a configurable value or when the rate of change of the difference in humidity between the bottom and top humidity sensors is above a configurable value in a very short amount of time, such as in 5, 10, 15, 30, 45, 60, 5-10, 15-30, or 30-60 seconds. Alternatively, in some example implementations, the detection device may be configured to send a signal when the load or weight of the diaper increases by a configurable threshold amount, such as 0.05, 0.1, 0.2, 0.3, 0.4, or 0.5 ounces or more, or a configurable threshold percentage, such as 25%, in a very short amount of time, such as in 5, 10, 15, 30, 45, 60, 5-10, 15-30, or 30-60 seconds. The thresholds may be centrally configured in the system and can be customized or localized based on the user's location. Additionally, the detection device may have Wi-Fi, Bluetooth low energy, Bluetooth, ZigBee, cellular data network, GPS, Satellite or other wireless capabilities to send and receive data. The two sets of sensors may be separated by a blocking layer such as a wireless signal blocking layer to allow more accurate measurements and to minimize radiation exposure to the diaper wearer. The detection device 201 may have a microcontroller or microprocessor 701 and battery 704.

In an alternate embodiment, where the detection device 201 may have multiple sensors of the same type such as multiple humidity sensors, gas sensors, temperature sensors, wetness sensors, load or weight sensors, and force sensors facing the inside of the diaper and may be configured to sense the concentration of gases, such as ammonia, methane and other gases, inside the diaper and measure other parameters, such as humidity, temperature, inside the diaper and multiple humidity sensors, gas sensors, temperature sensors, wetness sensors, load or weight sensors, and force sensors facing outside and away from the diaper, and that may be configured to sense the concentration of gases, such as ammonia, methane and other gases, outside the diaper and measure other parameters, such as humidity, temperature, outside the diaper. In some embodiments, multiple sensors of the same type may face each side, such as the inside and/or outside, of the diaper.

Figure 9:
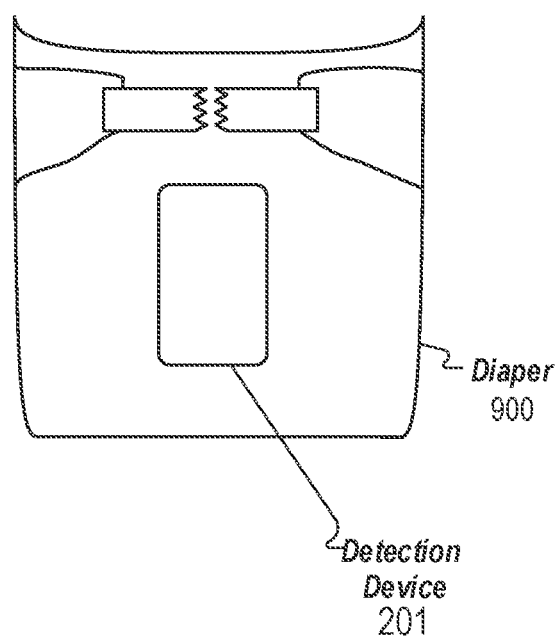
FIG. 9 illustrates a front view of the detection device that has been stuck on to or strapped on to the outside of the diaper.

FIG. 9 illustrates a front view of the detection device 201 that has been stuck on to or strapped on to the outside of the diaper 900. The detection device 201 may be stuck anywhere on the outside of the diaper 900 or placed in proximity to the wearer or to the diaper 900.

Figure 10:
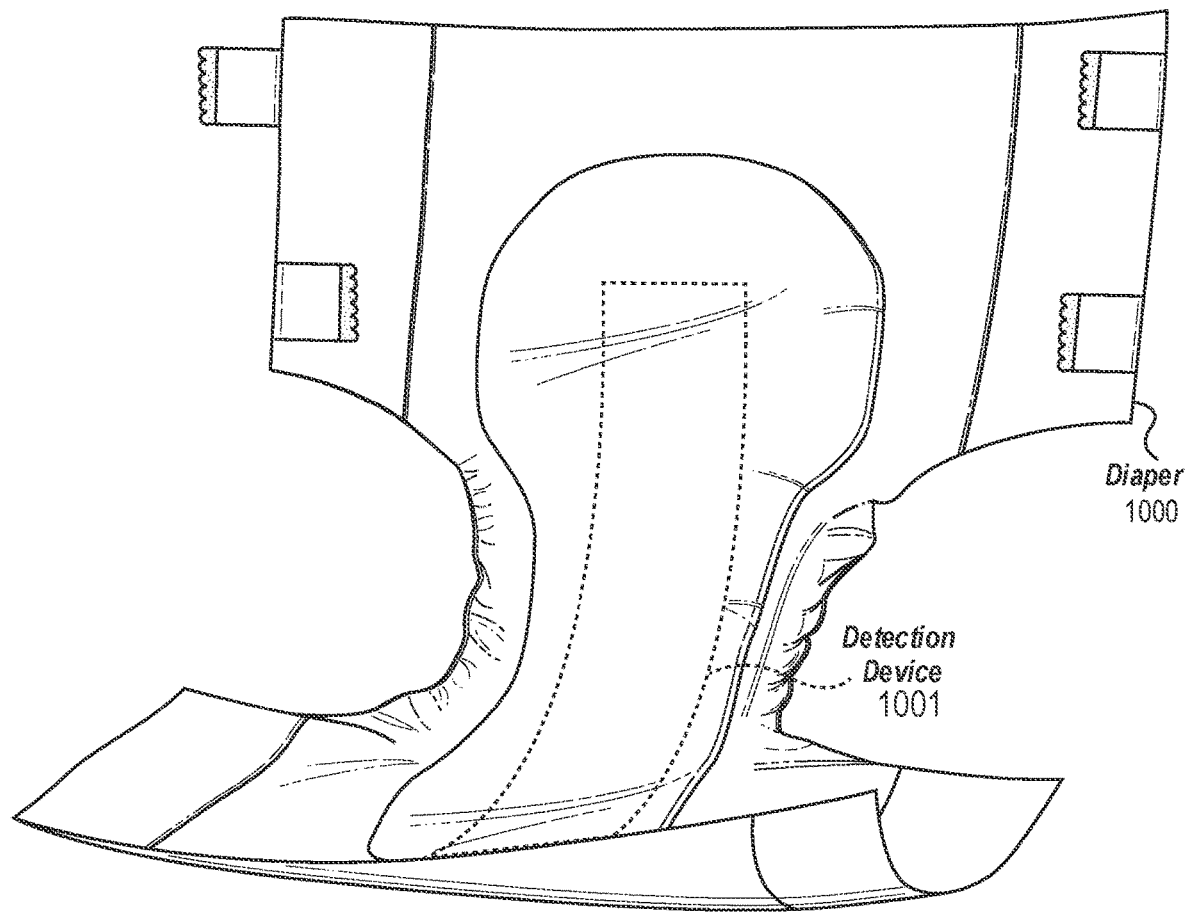
FIG. 10 illustrates a front view of the detection device that has been stuck on to or strapped on to the outside of the diaper along the front and back of the diaper.

FIG. 10 illustrates a front view of an elongated embodiment of the detection device 1001 that has been stuck on to or strapped on to the outside of the diaper 1000 along the front and back of the diaper. The elongated embodiment may attach to the front, back, and bottom of the diaper and wrap underneath the bottom of the diaper 1000. The elongated embodiment may be used for large diapers, such as adult diapers.

The various alternatives or combinations of the features shown or described herein may be incorporated into other embodiments and practiced and carried out in various ways which might be apparent to those skilled in this field and once the information herein is reviewed. Also, it is to be understood that the phraseology and terminology employed herein are for the purpose of description and should not be regarded as limiting in any fashion.

The invention claimed is:

1. A soiled diaper detection system for a diaper worn by a diaper wearer, the soiled diaper detection system comprising:
   a soiled diaper detection device with a vent and with two humidity sensors separated by a printed circuit board layer; wherein the humidity sensors are configured to measure humidity inside and outside of the diaper;
   one or more computer devices in communication with the soiled diaper detection device configured to generate requests to the soiled diaper detection device and process requests from the soiled diaper detection device, and store data received from the soiled diaper detection device;
   wherein the printed circuit board layer is configured to minimize radiation exposure to the diaper wearer; and
   wherein the soiled diaper detection device further comprises a learning-based system that uses humidity detection thresholds detected by the humidity sensors to adapt the soiled diaper detection device to the diaper wearer.

2. The soiled diaper detection system according to claim 1, wherein a first humidity sensor has a corresponding gas sensor configured to measure the rate of change of the difference in concentration of one or more gases.

3. The soiled diaper detection system according to claim 1, wherein each humidity sensor is configured to measure the rate of change of the difference in humidity between the inside and outside of the diaper.

4. The soiled diaper detection system according to claim 2, further comprising one or more additional sensors including at least one load or weight sensor or force sensor to measure the rate of change of the difference in weight of the diaper.

5. The soiled diaper detection system according to claim 1, further configured to send a signal when the rate of change of the difference in humidity between the inside and outside of the diaper exceeds a configurable value.

6. The soiled diaper detection system according to claim 2, further configured to send a signal when the rate of change of the difference in concentration of gases between the inside and outside of the diaper exceeds a configurable value.

7. The soiled diaper detection system according to claim 4, further configured to send a signal when the rate of change of the difference in weight of the diaper exceeds a configurable value within a minute.

8. The soiled diaper detection system according to claim 1, wherein-the learning-based system uses urination patterns to automatically adapt the soiled diaper detection device to the diaper wearer.

9. The soiled diaper detection system according to claim 2, further configured to send gas sensor output readings, humidity data and other data from one or more other sensors wirelessly to a hub.

10. The soiled diaper detection system according to claim 1, wherein the learning-based system automatically adapts the soiled diaper detection device based on the type of the diaper.

11. The soiled diaper detection system according to claim 1, wherein the soiled diaper detection device has circular vents on the top and bottom of the device.

12. The soiled diaper detection system according to claim 1, wherein the soiled diaper detection device connects wirelessly to a hub to send and receive humidity data and gas sensor readings.

13. The soiled diaper detection system according to claim 1, wherein the soiled diaper detection device goes along the front and back of the diaper.

14. The soiled diaper detection system according to claim 1, wherein the soiled diaper detection device has a removable and replaceable stick-on strap that keeps the top and bottom vents exposed.

15. The soiled diaper detection system according to claim 1, wherein the soiled diaper detection device has a battery and a humidity sensor that is configured to measure the rate of change of humidity, gas sensor and Bluetooth module that are fabricated onto an adhesive that sticks onto the outside of the diaper.

* * * * *